(12) United States Patent
Baetz et al.

(10) Patent No.: US 7,214,818 B2
(45) Date of Patent: May 8, 2007

(54) METHOD FOR SYNTHESIZING BISPHOSPHONATE

(75) Inventors: Friedrich Baetz, Einhausen (DE); Bernd Junghans, Edingen-Neckarhausen (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 11/252,668

(22) Filed: Oct. 18, 2005

(65) Prior Publication Data

US 2006/0094898 A1  May 4, 2006

(30) Foreign Application Priority Data

Oct. 29, 2004  (EP) .................. 04105407

(51) Int. Cl.
*C07F 9/38* (2006.01)
(52) U.S. Cl. ....................................... 562/13
(58) Field of Classification Search ................... 562/13
See application file for complete search history.

(56) References Cited

U.S. PATENT DOCUMENTS

| | | | |
|---|---|---|---|
| 3,919,321 A * | 11/1975 | Kyburz et al. | 568/326 |
| 4,220,611 A | 9/1980 | Wolf | |
| 4,876,339 A | 10/1989 | Blum et al. | |
| 4,927,814 A | 5/1990 | Gall et al. | |
| 4,942,157 A | 7/1990 | Gall et al. | |
| 5,002,937 A | 3/1991 | Bosies et al. | |

FOREIGN PATENT DOCUMENTS

| | | |
|---|---|---|
| EP | 252 504 | 1/1988 |
| EP | 332 068 | 9/1989 |
| EP | 350 002 | 1/1990 |
| EP | 402 152 | 12/1990 |
| WO | WO 01/57052 | 9/2001 |
| WO | WO 03/097655 | 11/2003 |

OTHER PUBLICATIONS

Widler, L., et al., Journal of Medicinal Chemistry, vol. 45, No. 17, pp. 3721-3738 (2002).
Hale, W. J., et al., Journal of the American Chemical Society, vol. 42, No. 1, pp. 107-116 (1920).
Galin, F.Z., et al., Bulletin of the Academy of Sciences of the USSR, Division of Chemical Science, vol. 37, No. 4, pp. 708-712 (1988).
Freifelder, M., et al., Journal of the American Chemical Society, vol. 80, No. 16, pp. 4320-4323 (1958).

* cited by examiner

*Primary Examiner*—Peter O'Sullivan
(74) *Attorney, Agent, or Firm*—George W. Johnston; Patricia S. Rocha-Tramaloni; David E. Wildman

(57) ABSTRACT

The invention relates to a novel multi step synthesis of 3-(N-methyl-N-pentyl) amino-1-hydroxypropane-1,1-diphosphonic acid, monosodium salt, monohydrate, of the formula

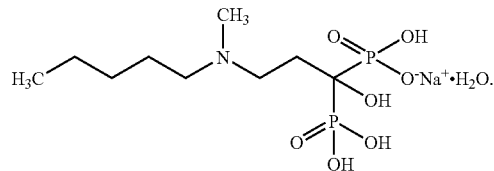

16 Claims, No Drawings

METHOD FOR SYNTHESIZING BISPHOSPHONATE

FIELD OF THE INVENTION

The present invention relates to a process for the preparation of 3-(N-methyl-N-pentyl) amino-1-hydroxypropane-1,1-diphosphonic acid, monosodium salt, monohydrate (hereinafter "ibandronate sodium") with the following formula

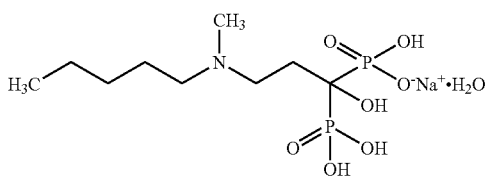

BACKGROUND OF THE INVENTION

Ibandronate sodium is one of the most potent antiresorptive drugs that directly inhibit osteoclast activity and present an effective pharmacologic alternative for controlling hypercalcemia. Ibandronate sodium binds to hydroxyapatite in calcified bone, rendering it resistant to hydrolytic dissolution by phosphatases, thereby inhibiting both normal and abnormal bone resorption. This drug increases bone mass and decreases the risk of fractures and is therefore particularly well adapted to bone and calcium metabolic diseases such as for instance osteoporosis or Paget's disease (EP-A 0252504).

For the preparation of bisphosphonic acids the following processes are known in the state of the art and have been considered.

EP 0402152 discloses the preparation of crystalline 4-amino-1-hydroxybutyllidene-1-bisphosphonic acid monosodium trihydrate, carried out in one step in presence of phosphorus trihalide, phosphorous acid and methane sulfonic acid. This process allows the reaction mixture to remain fluid.

WO 03/097655 discloses the preparation of a bisphosphonic acid including the step of combining a carboxylic acid with phosphorous acid and phosphoryl chloride in the presence of a diluent. The diluent includes aromatic hydrocarbons such as toluene, xylene and benzene or inert silicone fluids such as polydimethylsiloxane and polymethylphenylsiloxane.

However, the methods described in the art are not satisfactory with regard to yield and purity, in particular with respect to the synthesis of ibandronate sodium.

SUMMARY OF THE INVENTION

One object of the present invention therefore is to provide a new process for producing ibandronate sodium with high yields and with little residual by-products.

It has been found that this object could be achieved with the process of the present invention which comprises:
(a) condensing N-pentylamine with benzaldehyde to produce the N-benzylidene-N-pentylamine of formula II

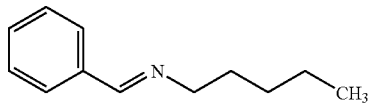

(b) transforming the N-benzylidene-N-pentylamine into N-methyl-N-pentylamine by reacting the N-benzylidene-N-pentylamine with a methylating agent
(c) reacting the N-methyl-N-pentylamine with methyl acrylate to form N-methyl-N-pentyl-β-alanine methylester of the formula III

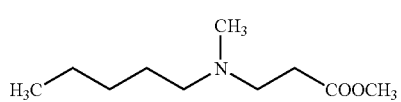

(d) converting the N-methyl-N-pentyl-β-alanine methyl ester to a compound of formula IV

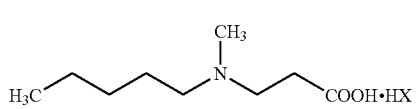

wherein X is a halogen, and
(e) bisphosphorylating the compound of formula IV by reacting the compound of formula IV with phosphoryl chloride and phosphorous acid subsequently forming the monosodium salt, monohydrate.

DETAILED DESCRIPTION OF THE INVENTION

All patents, patent applications, and publications disclosed herein are hereby incorporated by reference in their entirety. In case of a conflict in terminology, the present specification controls.

Generally, the first step of the process of the present invention comprises the condensation of N-pentylamine with benzaldehyde to produce the N-benzylidene-N-pentylamine of formula II.

This condensation can be carried out in a suitable solvent such as aliphatic alcohols, at a reaction temperature of 40° C. to 90° C., for example in methanol at 70° C. to 75° C.

Typically, the second step of the process of the present invention comprises the transformation of the N-benzylidene-N-pentylamine into the N-methyl-N-pentylamine with a methylating agent. Methylating agents such as methyl halogenides or dimethyl sulfate can be employed, but preferably dimethyl sulfate is used. The reaction can be conducted at a temperature of 80° C. to 110° C., preferably at 90° C. to 100° C. The benzaldehyde that is generated can be removed, for example, by steam distillation and the resulting N-methyl-N-pentylamine can be isolated from the aqueous phase by any means known to the skilled in the art such as by addition of a base and extraction of the basic solution with a suitable organic solvent such as an aliphatic ether, for example with diisopropylether. The product can be further purified, for instance, by distillation.

Generally, a third step of the process of the present invention involves reacting the N-methyl-N-pentylamine with methyl acrylate to form the N-methyl-N-pentyl-β-alanine methylester of formula III.

This reaction can be carried out in a suitable solvent such as an aliphatic alcohol, an aliphatic ether or an ether/alcohol mixture, for example in methanol at a reaction temperature of 10° C. to 65° C., or at 15° C. to 25° C. Isolation of the N-methyl-N-pentyl-β-alanine methyl ester can be performed by techniques known to the skilled in the art such as by distillation.

Hydrolysis of the N-methyl-N-pentyl-β-alanine methyl ester and formation of the hydrohalogenide produces the compound of the formula IV.

The hydrolysis can be performed by refluxing the N-methyl-N-pentyl-β-alanine methyl ester in a diluted mineral acid, but can also be performed by refluxing in water at least until no ester can be detected any further. Formation of the hydrohalogenide such as the hydrobromide or the hydrochloride, preferably of the hydrochloride (X=Cl) can be effected by addition of an aqueous solution of the appropriate mineral acid. The resulting N-methyl-N-pentyl-β-alanine hydrohalogenide, e.g., hydrochloride, can be isolated by distilling of the water and by a crystallization of the residue in a suitable solvent such as toluene/acetone or methyl ethyl ketone, preferably in methyl ethyl ketone.

Bisphosphorylating the compound of formula IV by means of phosphoryl chloride and phosphorous acid yields ibandronic acid, which can then be treated with the appropriate base to yield the monosodium salt, monohydrate.

The bisphosphorylation of the N-methyl-N-pentyl-β-alanine hydrochloride may take place either in the presence of a non aromatic solvent or with no solvent present. It is preferred to use a non aromatic solvent.

Suitable non aromatic solvents are, for example, phosphoric acid esters, phosphonic acid esters or carbonic acid esters. A preferred solvent is diethylcarbonate.

As phosphorylating agent a mixture of phosphoryl chloride and phosphorous acid is used. The molar ratio N-methyl-N-pentyl-β-alanine hydrochloride/phosphoryl chloride/phosphorous acid can range between 1:3:3 to 1:1.4:2.4, preferably 1:1.6:2.4 to 1:1.4:2.4

During the bisphosphorylation the reaction temperature is typically maintained in a range of from 60° C. to 100° C., preferably 80° C. to 90° C.

In case a non aromatic solvent is used it can be removed, for example, by addition of water and subsequent azeotropic distillation.

In order to isolate the monosodium salt, monohydrate of the 3-(N-methyl-N-pentyl) amino-1-hydroxypropane-1,1-diphosphonic acid the pH of the remaining aqueous reaction mixture is adjusted to a pH from about 3.5 to 6, preferably from 4.4 to 4.5 with an aqueous solution of a sodium-containing base, such as sodium hydroxide, at a temperature in the range of about 20° C. to 25° C.

The ibandronate sodium so obtained can be crystallized in suitable solvents such as aliphatic alcohols/water or aliphatic ketones/water, preferably in ethanol/water and acetone/water.

A further object of the present invention is to provide a process for the preparation of 3-(N-methyl-N-pentyl) amino-1-hydroxypropane-1,1-diphosphonic acid, monosodium salt, monohydrate of the formula I

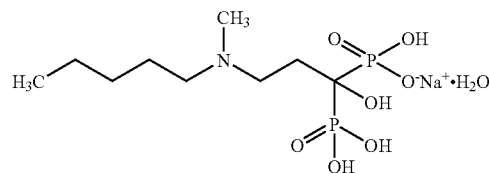

which process comprises the bisphosphorylation of the compound of formula IV

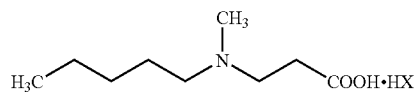

wherein X is a halogen, by reacting the compound of formula IV with phosphoryl chloride and phosphorous acid and subsequently forming the monosodium salt, monohydrate.

The preferred embodiments of this bisphosphorylation process are described above in paragraphs [17] to [22].

The process of the present invention allows the production of 3-(N-methyl-N-pentyl) amino-1-hydroxypropane-1, 1-diphosphonic acid, monosodium salt, monohydrate of the formula I in excellent yield and quality.

EXAMPLES a) Preparation of N-benzylidene-N-pentylamine 100 g (1.15 mol) N-pentylamine was added to 200 ml methanol at a temperature of 22° C. 121.8 g (1.15 mol) benzaldehyde was added. The mixture was refluxed and subsequently, methanol was distilled off. The residual N-benzylidene-N-pentylamine 199.8 g (99.4%) was used in the next step.

b) Preparation of N-methyl-N-pentylamine 60 g (475.7 mmol) dimethyl sulfate and 67 g (382.2 mmol) N-benzylidene-N-pentylamine were stirred at a temperature of 90–100° C. and 117 ml purified water was added to the mixture. The generated benzaldehyde was removed by steam distillation. 133 ml diisopropyl ether and 54 ml sodium hydroxide solution (50%) were added. The aqueous layer was separated. Diisopropyl ether was distilled off. 3.3 g sodium hydroxide flakes are added to the residue to bind residual water. The residue, crude N-methyl-N-pentylamine was purified by distillation (29.4 g; 76%).

c) Preparation of N-methyl-N-pentyl-β-alanine methyl ester 106 g (1.05 mol) N-methyl-N-pentylamine was added to cooled methanol of a temperature of 0–5° C. 108 g (1.25 mol) methyl acrylate was added to the solution and the mixture was stirred at room temperature for 8 hours. Then methanol was distilled off in vacuo and the residue was purified by distillation to obtain 188.6 g N-methyl-N-pentyl-β-alanine methyl ester (96.1%)

d) Preparation of N-methyl-N-pentyl-β-alanine hydrochloride 68.8 g (367.4 mmol) N-methyl-N-pentyl-β-alanine methyl ester was hydrolyzed by refluxing with 138 ml water. Then the water is partly distilled off and 83 ml (472.7 mmol) hydrochloric acid (19%) was added. Water was distilled off again and 230 ml methyl ethyl ketone was added to remove residual water by azeotropic distillation. The reaction mixture was then cooled to 24° C. The crystallized product was separated and washed with methyl ethyl ketone and subsequently dried in vacuo. 63.7 g (82.7%) N-methyl-N-pentyl-β-alanine hydrochloride were obtained.

e1) Preparation of 3-(N-methyl-N-pentyl) amino-1-hydroxypropane-1,1-diphosphonic acid, monosodium salt, monohydrate, in presence of diethyl carbonate as diluent 250 g (1.19 mol) N-methyl-N-pentyl-β-alanine hydrochloride, 233 g (2.84 mol) phosphorous acid, 151 ml (1.65 mol) phosphoryl chloride and 900 ml diethylcarbonate were heated stepwise to 80° C. After 2 hours reaction time under continued heating the mixture was cooled to 60° C. and 1733 ml water were added, followed by azeotropic distillation of diethylcarbonate/water at 90 to 101° C. 358 ml water was added, the mixture was refluxed and water was distilled off. 316 ml water were added and water was distilled off twice. Finally 2040 ml water were added and the residue was cooled to 24° C. The pH was adjusted at 23° C. with sodium hydroxide solution (50%) to 4.4. Thereafter, 1100 ml ethanol were added to start crystallization. The suspension was stirred for 8 hours at 21 to 22° C. Then the solid was separated, washed with 344 ml cold ethanol/purified water (7/5 V/V), subsequently with 344 ml acetone/purified water (5/2 V/V) and dried at 60° C.

315.6 g (73.7%) of the title product were obtained in the form of colorless crystals.

Assay (Complexometric Titration): 100.6% e2) Preparation of 3-(N-methyl-N-pentyl) amino-1-hydroxypropane-1,1-diphosphonic acid, monosodium salt, monohydrate 36.3 g (172.8 mmol) N-methyl-N-pentyl-β-alanine hydrochloride, 33.9 g (413.2 mmol) phosphorous acid, 22.75 ml (248.6 mmol) phosphoryl chloride were heated stepwise to 80° C. After 2 hours reaction time under continued heating the mixture was cooled to 60° C. and 251, 7 ml water were added. The mixture was refluxed and water was distilled off. 46 ml water were added and water was distilled off twice. 296.5 ml water were added and the residue was cooled to 24° C. The pH was adjusted with sodium hydroxide solution (50%) to 4.5 at 23° C. Thereafter, 159, 7 ml ethanol were added to start crystallization. The suspension was stirred for 8 hours at 21–22° C. Then the solid was separated, washed with 90 ml cold ethanol/purified water (3/2V/V), subsequently with 90 ml acetone/purified water (5/2 V/V) and dried at 60° C. 42.6 g (68.6%) of the title product were obtained in the form of colorless crystals.

Assay (Complexometric Titration): 99.8%

What is claimed is:
1. A process for the preparation of 3-(N-methyl-N-pentyl) amino-1-hydroxypropane-1,1-diphosphonic acid, monosodium salt, monohydrate of the formula I

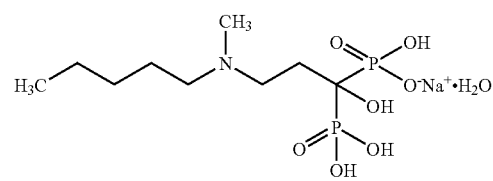

said process comprising:
(a) condensing N-pentylamine with benzaldehyde to produce the N-benzylidene-N-pentylamine of formula II

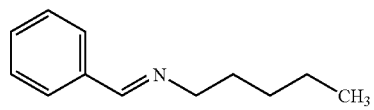

(b) transforming the N-benzylidene-N-pentylamine into N-methyl-N-pentylamine by reacting the N-benzylidene-N-pentylamine with a methylating agent
(c) reacting the N-methyl-N-pentylamine with methyl acrylate to form N-methyl-N-pentyl-β-alanine methylester of the formula III

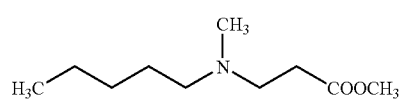

(d) converting the N-methyl-N-pentyl-□-alanine methyl ester to a compound of formula IV

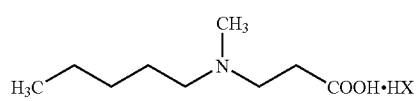

wherein X is a halogen, and
(e) bisphosphorylating the compound of formula IV by reacting the compound of formula IV with phosphoryl chloride and phosphorous acid subsequently forming the monosodium salt, monohydrate.
2. The process according to claim 1 wherein the condensing in step a) is performed using an aliphatic alcohol as a solvent and is conducted at a temperature of 40° C. to 90° C.
3. The process according to claim 2 wherein the transforming in step b) is performed at a temperature of 80° C. to 110° C.

4. The process according to claim 3 wherein the transforming in step b) is performed using dimethyl sulfate as the methylating agent.

5. The process according to claim 4 wherein the reacting in step c) is performed in a solvent selected from the group consisting of aliphatic alcohols, aliphatic ethers, and mixtures thereof at a reaction temperature of 10° C. to 65° C.

6. The process according to claim 5 wherein the bisphosphorylating in step e) is performed in the presence of a non-aromatic solvent.

7. The process according to claim 6 wherein the non-aromatic solvent is diethyl carbonate.

8. The process according to claim 7 wherein during the bisphosphorylating in step e) the molar ratio of N-methyl-N-pentyl-β-alanine hydrochloride:phosphoryl chloride:phosphorous acid ranges between 1:3:3 to 1:1.4:2.4.

9. The process according to claim 8 wherein the bisphosphorylating in step e) is conducted at a reaction temperature from 60° C. to 100° C.

10. The process according to claim 9 wherein the forming of the monosodium salt, monohydrate is effected by adjusting the pH of the aqueous reaction mixture to about 3.5 to 6 with an aqueous solution of a sodium-containing base.

11. A process for the preparation of 3-(N-methyl-N-pentyl)amino-1-hydroxypropane-1,1-diphosphonic acid, monosodium salt, monohydrate of the formula I

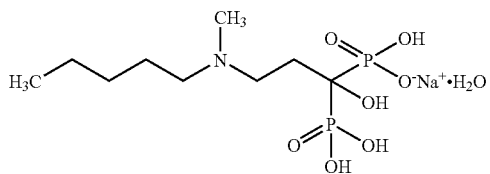

said process comprising bisphosphorylating a compound of formula IV

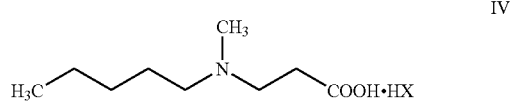

wherein X is a halogen,
by reacting the compound of formula IV with phosphoryl chloride and phosphorous acid and by subsequently forming the monosodium salt, monohydrate wherein the bisphosphorylating is performed in the absence of diluent or solvent or wherein the bisphosphorylating is performed in the presence of a non-aromatic solvent selected from the group consisting of phosphoric acid esters, phosphoric acid esters, and carbonic acid esters.

12. The process according to claim 11 wherein the bisphosphorylating is performed in the presence of solvent and the solvent is diethyl carbonate.

13. The process according to claim 11 wherein the molar ratio of N-methyl-N-pentyl-β-alanine hydrochloride:phosphorous oxychloride:phosphorus acid ranges between 1:3:3 to 1:1.4:2.4.

14. The process according to claim 11 wherein the bisphosphorylating is performed at reaction temperature of 60° C. to 100° C.

15. The process according to claim 11 wherein the forming of the monosodium salt, monohydrate is effected by adjusting the pH of the aqueous reaction mixture to about 3.5 to 6 with an aqueous solution of sodium hydroxide.

16. The process of claim 10, wherein the sodium-containing base is sodium hydroxide.

* * * * *

UNITED STATES PATENT AND TRADEMARK OFFICE
CERTIFICATE OF CORRECTION

PATENT NO. : 7,214,818 B2 Page 1 of 1
APPLICATION NO. : 11/252668
DATED : May 8, 2007
INVENTOR(S) : Friedrich Baetz et al.

It is certified that error appears in the above-identified patent and that said Letters Patent is hereby corrected as shown below:

Column 6, Claim 1, line 46, delete "N-methyl-N-pentyl-☐-alanine" and insert -- N-methyl-N-pentyl-ß-alanine --

Column 8, Claim 11, line 18, delete second occurrence "phosphoric acid esters," and insert -- phosphonic acid esters, --

Signed and Sealed this

Fourteenth Day of August, 2007

JON W. DUDAS
*Director of the United States Patent and Trademark Office*